United States Patent [19]

Goodwin et al.

[11] Patent Number: 4,824,985

[45] Date of Patent: Apr. 25, 1989

[54] NOVEL ROUTE TO $CA_8SI_4O_{12}CL_8$, ALKOXYCYCLOTETRASILOXANES, ARYLOXYCYCLOTETRASILOXANES, ALKYLCYCLOTETRASILOXANES AND ARYLCYCLOTETRASILOXANES FROM WOLLASTONITE ($CA SIO_3$)

[75] Inventors: George B. Goodwin, Mars, Pa.; Malcolm E. Kenney, Cleveland Heights, Ohio

[73] Assignee: Dow Corning Corporation, Midland, Mich.

[21] Appl. No.: 60,703

[22] Filed: Jun. 11, 1987

[51] Int. Cl.$^4$ .............................. C07F 7/08; C07F 7/18
[52] U.S. Cl. .................................... 556/460; 556/457; 556/461; 423/325; 423/326; 423/331; 423/332; 423/334
[58] Field of Search ...................... 556/460, 457, 461; 423/325, 326, 331, 332, 334

[56] References Cited

U.S. PATENT DOCUMENTS

Re. 784,216 5/1979 Kenney ................................. 556/456
4,309,557 1/1982 Compton et al. ..................... 556/453
4,717,773 1/1988 Kenney et al. ...................... 556/457

FOREIGN PATENT DOCUMENTS 732533 6/1955 United Kingdom ........ 556/457 UX

OTHER PUBLICATIONS

Calhoun and Masson, J.C.S. Dalton, 1980, p. 1282.
Bleiman and Mercier, Inorg. Chem., 1975, 14, p. 2853.
Chukhlantsev, Dokl. Phys. Chem. (Eng. Trans.) 1979, 246, p. 530.
Kuroda, et al., Polymer, 1978, vol. 19, Nov., p. 1300–1302.
Winkler et al., Z. Anorg. Allg. Chemie, 504, 89–94, 1983.
Kenney, et al., Polym. Prep. Am. Chem. Soc. Dir. Polym. Chem., 1986, 27, p. 107.

*Primary Examiner*—Paul F. Shaver
*Attorney, Agent, or Firm*—James E. Bittell

[57] ABSTRACT

The present invention relates to a process for the preparation of alkoxy, aryloxy, alkyl, and aryl cyclotetrasiloxanes from a metal silicate halide salt, $Ca_8Si_4O_{12}Cl_8$.

21 Claims, No Drawings

NOVEL ROUTE TO CA₈SI₄O₁₂CL₈, ALKOXYCYCLOTETRASILOXANES, ARYLOXYCYCLOTETRASILOXANES, ALKYLCYCLOTETRASILOXANES AND ARYLCYCLOTETRASILOXANES FROM WOLLASTONITE (CA SIO₃)

FIELD OF THE INVENTION

This invention relates generally to a process for the preparation of alkoxy, aryloxy, alkyl, and aryl cyclotetrasiloxanes, and more particularly to a process for the formation of octaethoxycyclotetrasiloxane and octamethylcyclotetrasiloxane from a metal silicate halide salt, $Ca_8Si_4O_{12}Cl_8$, which is derived from wollastonite, $CaSiO_3$.

BACKGROUND OF THE INVENTION

The process traditionally used for the commercial production of the economically most important alkoxysilanes involves two main steps. The first of these entails the synthesis of silicon tetrachloride. This can be made in a variety of ways. In one, silica is reduced to elemental silicon with carbon in an electric arc furnace, and this is then chlorinated with elemental chlorine. The reduction of the silica to silicon consumes large amounts of electrical energy, a fact reflected in the cost of the silicon. Once the silicon tetrachloride has been prepared, it is reacted with an alcohol, such as ethanol, to produce the tetraalkoxysilane:

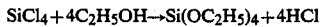

An economically important alkoxysiloxane is made by the hydrolysis of tetraethoxysilane. It contains about 40 wt% $SiO_2$ and is often called ethyl silicate 40.

Various alkoxysilanes can be made by a transesterification process:

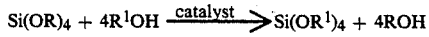

Among the catalysts used for this process are sodium alkoxides. This process is used mainly for the preparation of the alkoxysilanes of alcohols with relatively high boiling points.

The so-called direct process for producing alkoxysiloxanes involves two steps. In the first, silica is reduced to elemental silicon with carbon in an electric arc furnace. Then it is treated with an alcohol, such as ethanol, to produce the tetraalkoxysilane. Both the traditional and direct processes are energy intensive. They require complete scission of the silicon-oxygen linkages and formation of new ones.

Calhoun and Masson (J. C. S. Dalton 1980, 1282) found that hexaisopropoxycyclotrisiloxane is formed as a very minor byproduct when pseudowollastonite, $Ca_3Si_3O_9$, is treated with trimethylchlorosilane, hexamethyldisiloxane, and isopropyl alcohol. This work shows that alkoxysiloxanes can be made from silicates as byproducts under the reaction conditions used by the authors.

It has also been shown by Bleiman and Mercier (Inorg. Chem. 1975, 14, 2853) that the sheet silicate chrysotile, $Mg_3Si_2O_5(OH)_4$, (common asbestos) can be partially converted to a partially esterified sheet silicate by treating it with hydrochloric acid and isopropyl alcohol and then treating the resulting material with allyl alcohol and pyridine.

It has been reported by the present inventors, Polym. Prepr. Am. Chem. Soc. Div. Polym. Chem. 1986, 27, 107, that wollastonite, $CaSiO_3$, can be heated at a temperature below its melting point for an extended period of time to produce the cyclotrisilicate, pseudowollastonite ($Ca_3Si_3O_9$), which upon treatment with acid and ethanol produces octaethoxytrisiloxane and hexaethoxycyclotrisiloxane. It was also taught by the present inventors in the Polym. Prepr. Am. Chem. Soc. publication that high yields of specific siloxane species can be obtained depending on the crystal structure of the silicate starting material. For example, it has been taught by the present inventors that $Ca_3Si_3O_9$ has the potential to give high yields of the cyclic trimeric siloxane upon treatment with acids and alcohols.

Earlier work by the present inventors utilized a metal salt of silicon dioxide, a cyclic silicate, or a linear oligomeric silicate, but did not proceed through the specific and preferred cyclic metal halide salt intermediate described herein.

Chukhlantsev, in Dokl. Phys. Chem. (Engl. Transl.) 1979, 246, p.530, reported work related to the synthesis of the metal silicate halide salt, $Ca_8Si_4O_{12}Cl_8$, from quartz but not from wollastonite. Chukhlantsev was directed primarily to the formation of $Ca_2SiO_3Cl_2$.

United Kingdom patent number 732,533, issued to Wacker-Chemie G.m.b.H. on June 29, 1955, teaches and claims the reaction of a polysiloxane containing silicon-bonded hydrocarbon radicals and alkoxy or aryloxy groups with sodium, lithium, calcium, magnesium or zinc, or a mixture thereof, and a halogenated hydrocarbon.

U.S. Pat. No. 4,309,557, issued on Jan. 5, 1982 to Compton et al., teaches and claims the process for displacing alkoxy groups on linear oligomeric siloxanes by a Grignard reaction to produce short chain, linear alkylated siloxanes.

Kuroda et al. reported the synthesis of polyorganosiloxane retaining the silicate framework from inosilicate mineral, para-wollastonite, by trimethylsilylation. Kuroda et al., Polymer, 1978, vol. 19, November, p. 1300–1302.

The present inventors filed on Oct. 4, 1985, a related patent application titled "Silicate Esters And Organosilicon Compounds", Ser. No. 784,216.

A need exists for an economic process not based on complete reduction and subsequent re-oxidation of silicon, which will produce in high yield cyclic tetrameric alkoxysiloxanes and cyclic tetrameric alkylsiloxanes.

SUMMARY OF THE INVENTION

It has been discovered that cyclic alkoxysiloxanes can be prepared by suspending a metal silicate halide salt, for example, derived from wollastonite, in an alcohol, treating the suspension with a strong acid such as hydrochloric acid, heating the mixture, removing the low-boiling components from the resulting mixture, and then isolating the cycloalkoxysiloxane from the residue. The metal silicate halide salt starting material may be either natural or synthetic. It is notable in the process of the invention that when alkoxysiloxanes are made, the basic silicon-oxygen backbone of the ionic salt is preserved. It is also notable that the silicon remains in an oxidized state throughout the process of the present invention. It has also been discovered that alkoxycyclotetrasiloxanes produced by the present invention can be alkylated or arylated with Grignard alkylating or arylating reagents to produce octaalkyl- or octaarylcyclotetrasiloxanes in high yields.

DETAILED DESCRIPTION OF THE INVENTION

It is an object of the present invention to provide a process for the production of alkoxycyclotetrasiloxanes from a readily-available metal silicate, or from a metal silicate and silica, by way of an alkaline metal silicate halide salt. It is a further object of the present invention to provide a process for producing alkoxycyclotetrasiloxanes whereby the alkoxycyclotetrasiloxanes produced have silicon-oxygen arrangements identical to that of the alkaline metal silicate halide salt. Yet another object of the present invention is to provide a process for preparing the alkaline metal silicate halide salt from wollastonite, $CaSiO_3$. A further object of the present invention is to provide a process for preparing the alkaline metal halide salt, and subsequent alkoxy-, aryloxy, alkyl-, and arylcyclotetrasiloxanes from quartz.

It is a further object of the present invention to produce alkoxycyclotetrasiloxanes and aryloxycyclotetrasiloxanes from a calcium silicate halide salt, including, but not limited to, $Ca_8Si_4O_{12}Cl_8$.

It is a further object of the present invention to produce alkoxycyclotetrasiloxanes from a strontium silicate halide salt, including, but not limited to, $Sr_8Si_4O_{12}Cl_8$. Both wollastonite and the $Ca_8Si_4O_{12}Cl_8$ salt are known materials, the former being a naturally-occurring silicate, and the latter, and materials similar to it, having been previously synthesized from alpha-quartz, but not from wollastonite. (vide Chukhlantsev, supra.) The strontium silicate, $Sr_8Si_4O_{12}Cl_8$, is also known. (vide Winkler et al., Z. Anorg. Allg. Chem., 504, 89-94, 1983)

Another object of the present invention is to provide a process for preparing alkylcyclotetrasiloxanes and arylcyclotetrasiloxanes from alkoxycyclotetrasiloxanes and aryloxycyclotetrasiloxanes by the Grignard process without cleaving the preformed and desired tetrameric silicate ring. It is yet another object of the present invention to provide a process for preparing alkylcyclotetrasiloxanes from alkaline metal silicate halide salts, such as, but not limited to, $Ca_8Si_4O_{12}Cl_8$. By "alkaline metal silicate halide salts" in the present invention is meant those halide salts of Group I metals and Group II metals.

Still another object of the present invention is to provide a process for preparing alkylcyclotetrasiloxanes from wollastonite, which process requires the formation of a cyclic alkaline metal tetrameric silicate salt from the silicate structure of wollastonite.

The present invention relates to a process comprising (A) mixing wollastonite with an alkaline metal halide or alkaline metal halide hydrate, or mixture thereof; (B) calcining the mixture; and (C) isolating the alkaline metal cyclic silicate halide salt.

A preferred embodiment of the process of the present invention is calcining the mixture to a temperature between 400 and 1300 degrees Centigrade, and more preferably to a temperature between 500 and 800 degrees Centigrade.

The present invention further relates to a process for preparing an alkoxycyclotetrasiloxane of the general formula

[(RO)$_2$SiO]$_4$ wherein, R is an alkyl group of 1 to 8 carbon atoms, from wollastonite or other suitable silicate with, if necessary for the production of the desired $[Si_4O_{12}]^{8-}$ cyclic ion, silica or calcium oxide or carbonate, which process comprises:

(A) mixing wollastonite or other suitable silicate and, if necessary, silica or calcium oxide or carbonate, with an alkaline halide, or alkaline halide hydrate or a mixture thereof;

(B) calcining the mixture to produce an alkaline metal cyclic silicate halide salt;

(C) treating the alkaline metal cyclic silicate halide salt with an anhydrous or aqueous acidic alcoholic solution, wherein the alcohol of the acidic alcoholic solution has 1 to 8 carbon atoms, and wherein the acid used to acidify the acidic alcoholic solution is selected from the group consisting of organic and inorganic acids to form an alcoholic mixture;

(D) removing low-boiling components from said alcoholic mixture; and, (E) isolating the alkoxycyclotetrasiloxane from the residue of (D).

The invention also relates to a process for preparing organocyclotetrasiloxanes having the general formula

[(R$^2$)$_2$SiO]$_4$ wherein, R$^2$ is an alkyl group of 1 to 10 carbon atoms or an aryl group of 6 to 10 carbon atoms, from wollastonite, or other suitable silicate with, if necessary for the production of the desired $[Si_4O_{12}]^{8-}$ cyclic ion, silica or calcium oxide or carbonate, the process comprising:

(A) mixing wollastonite or other suitable silicate and, if necessary, silica or calcium oxide or calcium carbonate, with an alkaline halide, alkaline halide hydrate, or a mixture thereof;

(B) calcining the mixture to produce an alkaline metal cyclic silicate halide salt;

(C) treating the alkaline metal cyclic silicate halide salt from (B) with an anhydrous or aqueous acidic alcoholic solution, wherein the acid used to acidify the acidic alcoholic solution is selected from the group consisting of organic and inorganic acids, to form an alcoholic mixture;

(D) removing low-boiling components from said alcoholic mixture to produce the alkoxycyclotetrasiloxane;

(E) producing the organocyclotetrasiloxane by treating the alkoxycyclotetrasiloxane with a solution of a Grignard reagent selected from the group of Grignard reagents represented by the formula R$^2$MgX, where R$^2$ represents an alkyl group of 1 to 10 carbon atoms or an aryl group of 6 to 10 carbon atoms, and X represents a halogen selected from the group consisting of chlorine and bromine; and (G) isolating the organocyclotetrasiloxane.

The invention still further relates to a process for preparing the cyclic metal silicate ion $[Si_4O_{12}]^{8-}$ which comprises mixing wollastonite or other suitable silicate with, if necessary for the production of the desired $[Si_4O_{12}]^{8-}$ cyclic ion, silica and calcium oxide or calcium carbonate, and an alkaline metal halide, an alkaline metal halide hydrate, or a mixture of alkaline metal halides and alkaline metal halide hydrates, and calcining the resulting mixture until $[Si_4O_{12}]^{8-}$ is formed. The inventors believe, but do not wish to be held to the theory that, the $[Si_4O_{12}]^{8-}$ cyclic ion forms in the presence of $CaCl_2$ formed from $CaCl_2 \cdot 2H_2O$, but not in the presence of $CaCl_2 \cdot 2H_2O$ itself. The formation of the cyclic ion $[Si_4O_{12}]^{8-}$ can thus result from the presence of calcium chloride hydrates, including, for example, $CaCl_2 \cdot 2H_2O$, $CaCl_2 \cdot 6H_2O$, $CaCl_2 \cdot 4H_2O$, $CaCl_2 \cdot 2H_2O$ and $CaCl_2 \cdot H_2O$, among others. By "alkaline metal halide hydrate" in the present invention is meant the commonly occurring hydrates, such as, but not limited to, the mono-, di-, and trihydrates of alkaline metal halides.

By the present invention, a readily-available alkaline metal silicate is converted by appropriate treatment into an alkaline metal silicate halide salt with an ion framework that is the same as that of the alkoxysiloxane ester to be prepared. This alkaline metal silicate halide salt, possessing the cyclic ion, $[Si_4O_{12}]^{8-}$, is then converted into the desired ester by a process that entails extraction of the ion and grafting of the alkoxy groups.

The inventors believe that what is needed for the synthesis of the $Ca_8Si_4O_{12}Cl_8$ salt is a source of $Ca^{++}$, $Si^{4+}$, $O^{2-}$ and $Cl^-$ in appropriate proportions. Therefore, other silicates, quartz, or combinations of silicates and silica or calcium oxide or carbonate can be used, for example, $CaSiO_4$ and $SiO_2$ or $Ca_3SiO_5$ and $SiO_2$, where such combinations facilitate the production of the $Ca_8Si_4O_{12}Cl_8$ salt, or more importantly, the desired $[Si_4O_{12}]^{8-}$ cyclic ion. The invention therefore also relates to a process comprising (A) mixing a silicate precursor selected from the group consisting of a mixture of an alkaline metal silicate and silica; silica and alkaline metal carbonate or oxide, with an alkaline halide, alkaline halide hydrate, or mixture thereof, (B) calcining the mixture; and (C) isolating the alkaline metal cyclic silicate halide salt.

The cation of the alkaline metal silicate halide salt need not be limited to calcium, but may be independently selected from the group consisting of strontium, lithium, sodium, magnesium, potassium, calcium, barium, or combinations thereof. The halogen of the halide salt can be selected from the group consisting of fluorine, chlorine, bromine and iodine.

A preferred embodiment of the present invention utilizes wollastonite to produce $Ca_8Si_4O_{12}Cl_8$, which in turn, is preferably treated with hydrochloric acid and ethanol to produce octaethoxycyclotetrasiloxane, which is then preferably alkylated with $CH_3MgCl$ Grignard reagent to yield octamethylcyclotetrasiloxane.

An interesting feature of the process of the present invention is the preparation of the desired backbone first and then the placement of the desired pendent groups on this backbone. This is, of course, in contrast to the sequence usually used in oligomer and polymer siloxane synthesis.

According to the instant invention, the synthesis of $[(C_2H_5O)_2SiO]_4$ from wollastonite has three main parts. These are (1) the heating of the mixture of wollastonite and $CaCl_2 \cdot 2H_2O$ to produce the metal silicate halide salt $Ca_8Si_4O_{12}Cl_8$, (2) the stirring of the mixture of $Ca_8Si_4O_{12}Cl_8$, HCl, ethanol, and toluene, and (3) the extraction and distillation of the reaction product. In the first part, the cyclic $[Si_4O_{12}]^{8-}$ ion of the $Ca_8Si_4O_{12}Cl_8$ is formed from the linear metasilicate ion present in wollastonite, in the second part this cyclic $[Si_4O_{12}]^{8-}$ ion is liberated, and in the third part it is converted to $[(C_2H_5O)_2SiO]_4$.

A unique and unexpected aspect of the process of the present invention is the high percentage of cyclic tetrameric siloxane produced as a major product as opposed to its production as a minor product in the earlier work of the inventors using pseudowollastonite. In pseudowollastonite, the ion is $[Si_3O_9]^{6-}$. Thus any $[(C_2H_5O)_2SiO]_4$ formed from pseudowollastonite is formed by cleavage and rearrangement. The $[(C_2H_5O)_2SiO]_4$ in the pseudowollastonite product is a rearrangement product and not a structure preservation product, as is the $[(C_2H_5O)_2SiO]_4$ from the $Ca_8Si_4O_{12}Cl_8$ product of the present invention. The cyclic tetrameric structure of the $[Si_4O_{12}]^{8-}$ cyclic ion is preserved during the reactions of the present invention and retained in the cyclic alkoxysiloxane product.

By substituting an alkyl or aryl alcohol for ethanol, alkoxycyclotetrasiloxanes and aryloxycyclotetrasiloxanes are produced by the process of the present invention.

Earlier work by the inventors directed toward the synthesis of cyclic polysiloxanes suffered from the inability to find natural or readily-preparable silicates which contain the $[Si_4O_{12}]^{8-}$ ion, are soluble in acidic reaction conditions, and do not contain toxic cations. It has been found that alkaline salts of the halide cyclic silicates have the desired and improved acid solubility and can be made easily. In the present invention an acid-soluble source of the desired $[Si_4O_{12}]^{8-}$ ring is provided by the conversion of wollastonite to $Ca_8Si_4O_{12}Cl_8$. It is important to the present invention that the irregular heptacoordination of the $Ca^{++}$ ion in the $Ca_8Si_4O_{12}Cl_8$ salt, and the possession of three $Ca^{++}$—$Cl^-$ bonds per $Ca^{++}$, probably contribute to the ability of the salt to undergo alkoxylation or aryloxylation under relatively mild conditions so that the cyclic framework remains intact.

The use of starting materials possessing twelve-membered rings did not yield $[(C_3H_5O)_2SiO]_4$ because the twelve-membered rings did not react to give as intermediates $[(HO)_2SiO]_4$ or partially esterified $[(HO)_2SiO]_4$. The $Si_6O_{18}^{12-}$ ion would be expected to produce $[(HO)_2SiO]_6$ if it yielded a simple cyclic compound. It would produce $[(HO)_2SiO]_4$ only if it, or if its partial ester, rearranged. The $[SiO_4]^{4-}$ ion did produce $[(C_2H_5O)_3SiO]_4$ because in solution it reacted to give $[(HO)_2SiO]_4$, or partially esterified $[(HO)_2SiO]_4$, which reacted with the alcohol. However, this is a different process than the process described herein for $Ca_8Si_4O_{12}Cl_8$. Unexpectedly, however, the eight-membered rings of $Ca_8Si_4O_{12}Cl_8$ produced from wollastonite are shown by the present invention to be an excellent source of acid-soluble starting material which, upon treatment with acid in the presence of an alcohol, will produce high yields of the desired cyclic tetrameric alkoxysiloxane. With $[SiO_2]^{4-}$, the formation of the ring takes place in solution, while in the present invention using $[Si_4O_{12}]^{8-}$, the formation of the ring takes place during the synthesis of the silicate. The process is thus distinct from the prior art. It is believed that it has not been previously taught to use wollastonite to produce $Ca_8Si_4O_{12}Cl_8$ nor has it been previously taught to use the preformed cyclic ion of $Ca_8Si_4O_{12}Cl_8$ to produce alkoxycyclotetrasiloxanes or aryloxycyclotetrasiloxanes.

The present invention is directed toward processes for preparing alkoxycyclotetrasiloxanes, aryloxycyclotetrasiloxanes, arylcyclotetrasiloxanes, and alkylcyclotetrasiloxanes from alkaline metal silicate halide salts possessing the cyclic tetrasilicate structure $[Si_4O_{12}]^{8-}$. Unlike the prior art, the process of the present invention isomerizes the linear polysilicate ion of wollastonite or isomerizes or rearranges the ions of other silicates or silica, with or without additional calcium oxide, to a cyclic metasilicate ion in the first step, and does not rearrange an orthosilicate ion in the acid-alcohol step.

The inventors believe, but do not limit the invention to the belief, that the process of the present invention includes the following steps $$CaCl_2 \cdot 2H_2O \rightarrow CaCl_2 \qquad (1)$$

$$CaSiO_3 + CaCl_2 \rightarrow Ca_8Si_4O_{12}Cl_8 \qquad (2)$$

$$Ca_8Si_4O_{12}Cl_8 + HCl + ROH \rightarrow [(RO)_2SiO]_4 \qquad (3)$$
$$[(RO)_2SiO]_4 + 2R^2MgCl \rightarrow [R^2{}_2SiO]_4 \qquad (4)$$

where $R^2$ is defined as above.

The alkoxycyclotetrasiloxane, which is produced as described above from wollastonite and the metal silicate halide salt, can be alkylated or arylated by the Grignard process to produce commercially important alkyl or aryl polysiloxanes. The steps represented above include the isomerization of a linear polysilicate ion from wollastonite, $CaSiO_3$, to form a cyclic metasilicate ion of the halide salt, $Ca_8Si_4O_{12}Cl_8$. This ion is then esterified with an alcohol and an acid to an alkoxycyclotetrasiloxane.

It is an unexpected discovery of the present invention that the alkoxycyclotetrasiloxanes and aryloxycyclotetrasiloxanes of the present invention can be converted to the alkylated or arylated cyclotetrasiloxane by the Grignard process in high yield without ring cleavage.

The alkylcyclotetrasiloxanes, produced by the Grignard process as applied in the process of the present invention, can be isomerized or equilibrated by techniques known to those skilled in the art to produce the linear polydialkylsiloxanes which are of such high commercial significance.

A major advantage of the present invention over the prior art of Grignard alkylation is the high yield of alkylated cyclotetrasiloxane obtained. In earlier attempts, good yields of $[(CH_3)_2SiO]_4$ from the gamma-$Ca_2SiO_4$ reaction were not obtained because the amount of $[(CH_3CH_2O)_2SiO]_4$ in the alkoxy mixture was not high. Good yields of $[(CH_3)_2SiO]_6$ from the $Na_4Ca_4Si_6O_{18}$ reaction were not obtained because the amount of $[(CH_3CH_2O)_2SiO]_6$ in the alkoxy mixture was very low. The feature of the instant invention is that the amount of $[(CH_3CH_2O)_2SiO]_4$ in the alkoxy mixture from $Ca_8Si_4O_{12}Cl_8$ is high and thus the yield of $[(CH_3)_2SiO]_4$ is high. Grignard alkylation reaction conditions normally cause significant amounts of cleavage to occur in siloxane chains, whereby the reaction products are the result of cleavage, and include $R_3SiOH$ if $(R_2SiO)_n$ is the starting material. By contrast, the instant invention preserves the cyclotetrasiloxane ring structure intact while alkylating or arylating the ring.

Furthermore, prior art Grignard alkylation reaction syntheses, when less vigorous reaction conditions are used, frequently result in incomplete alkylation, whereby the reaction product is a mixture of partially-alkylated siloxanes, condensation products, and remaining alkoxysiloxanes, among other chemical species.

In the method of the instant invention for the preparation of alkoxycyclotetrasiloxanes or aryloxycyclotetrasiloxanes, the starting alkaline metal silicate halide salt provides the silicon framework upon which the subsequent steps are carried out. Throughout the process in all cases the silicon remains in an oxidized condition.

As a second step in the process of the present invention, the cyclic metal silicate halide salt, $Ca_8Si_4O_{12}Cl_8$, produced from wollastonite or other suitable silicate with, if necessary for the production of the desired $[Si_4O_{12}]^{8-}$ cyclic ion, silica or calcium oxide or calcium carbonate, is treated with an anhydrous or aqueous strong acid in an alcohol solution. Although the cyclic alkaline metal silicate halide salt may be directly contacted with the acid solution, it is a preferred embodiment of the present invention to suspend the alkaline metal silicate halide salt as a powder or other finely-divided form in an alcohol to facilitate the reaction. All of the $C_{1-8}$ alcohols are satisfactory for this purpose, although methanol, ethanol, n-propanol, isopropanol, n-butanol, and sec-butanol are preferred. The acid solution is then advantageously prepared using the same alcohol used for the metal silicate halide salt suspension.

A preferred embodiment of the alkaline metal silicate salt useful in the present invention to prepare both the alkoxycyclotetrasiloxanes and the alkylcyclotetrasiloxanes is $Ca_8Si_4O_{12}Cl_8$.

The acid used for the step of rendering labile the pendent oxygen atoms on the starting silicate is preferably a strong acid selected from the group consisting of organic and inorganic acids. The preferred acids are hydrochloric, hydrobromic, sulfuric, phosphoric, and oxalic acids, with hydrochloric acid being more preferred for ease of handling. The acid may be anhydrous or aqueous, organic or inorganic, and its concentration in the solution may vary over a wide range, from 0.01 to 18M, and still be useful. However, sufficient acid should be present in the solution containing the metal silicate halide salt to ensure displacement of all or nearly all of the alkaline metal ions of the alkaline metal silicate halide salt.

The temperature of the solution during the initial period of contact between the acid and the alkaline metal silicate halide salt should ideally be maintained in a range between about $-30$ degrees Centigrade and the boiling point of the alcohol. A lower temperature reduces the incidence of undesirable side reactions in the preparation of the alkoxycyclotetrasiloxanes having silicon-oxygen frameworks based on those of the parent alkaline metal silicate ion, but too low a temperature leads to long reaction times. A temperature between 0 and 25 degrees Centigrade is preferred.

After the acid and the alkaline metal silicate halide salt have been thoroughly mixed and the reaction is proceeding, it may be necessary to heat the reaction and to remove byproduct water to allow the reaction to go to completion. The inventors believe that the water removal can be accomplished by standard techniques such as use of a desiccant or molecular sieves. However, an azeotropic distillation is most efficient and is preferred. Several of the alcohols which may be used as a reactant form azeotropes with water, and the reaction mixture can be heated to strip off water and other low-boiling components without further treatment. Alternatively, an otherwise inert azeotrope former can be added to the reaction mixture prior to distillation. Toluene or chloroform have been found to be well-suited for this purpose.

After the initial reaction between the silicate and the acid-alcohol mixture is complete, it is desirable to separate the reaction products from the byproduct salts. This is most easily accomplished by filtration of the mixture and extraction of the salts formed with an organic solvent. Hexane, heptane, and pentane have been found to be most useful for this purpose, with pentane being the preferred solvent. The organic solvent extract and the filtrate are combined, concentrated, treated with more acid and alcohol, if desired, and then the product is isolated. The isolations are carried out using conventional methods such as evaporation or distillation.

The third step of the process of the instant invention directed toward the preparation of alkylcyclotetrasiloxanes is the use of a Grignard alkylating or arylating agent to replace the alkoxy or aryloxy groups with alkyl or aryl groups. In the present invention Grignard alkylating reagents possessing 1 to 10 carbon atoms are preferred and Grignard arylating reagents possessing 6 to 10 carbon atoms are preferred.

Another difficulty experienced in earlier attempts to alkylate alkoxycyclosiloxanes with Grignard reagents is that if the conditions are not vigorous enough, little or no alkylation will result.

It is therefore unexpected that by the present invention alkylcyclotetrasiloxanes can be produced in high yields by reacting a Grignard reagent with an alkoxycyclotetrasiloxane. The cyclic tetrameric structure is not only preserved during the alkylation process of the present invention, but is efficiently alkylated by the Grignard reaction, without excessive cleavage or rearrangement.

A critical aspect of the process of the present invention is the persistence of the main structural features of the cyclic silicate backbone of the parent silicate throughout the hydroylsis and substitution steps. A key to this persistence is the combination of stability and lability characteristic of the alkoxy groups of alkoxysiloxanes. It is this combination that allows for the selective scission of unwanted oxygen atoms from the silicate backbone. Another advantage of the process of the present invention is its avoidance of full depolymerization of the metal silicate structure, avoidance of reduction and oxidation steps, and avoidance of chlorosilanes. In addition, the process produces high yields of cyclic tetrameric alkoxysiloxanes. Yet another useful advantage of the processes of the present invention is the production in high yields of alkylcyclotetrasiloxanes and arylcyclotetrasiloxanes.

The alkoxycyclotetrasiloxane, alkylcyclotetrasiloxane, aryloxycyclotetrasiloxane, and arylcyclotetrasiloxane products isolated from the processes of the present invention are liquids or solids. When pure, they are colorless and have moderate chemical reactivity. For example, the alkoxycyclotetrasiloxanes hydrolyze slowly in the presence of water. The products of the processes of the present invention can be used as synthetic intermediates, hydraulic fluids, heat-transfer media, and binders, among other things.

EXAMPLE 1

Preparation of $Ca_8Si_4O_{12}Cl_8$ from $CaSiO_3$ (Wollastonite)

A mixture of wollastonite, ($CaSiO_3$, obtained from Mexico, powdered, 60.0 grams) and $CaCl_2 \cdot 2H_2O$ (152 grams) contained in two platinum dishes was placed in an inert-atmosphere furnace chamber. Under a nitrogen flow, the part of this chamber containing the mixture was heated slowly to 775 degrees Centigrade and held at this temperature for 16.5 hours. During this step, the nitrogen flow was maintained at a moderate rate (approximately 250 mL/minute) until the rapid evolution of water had ceased and then the flow was reduced to a slower rate (approximately 10 mL/minute). The resulting solid was removed, crushed with a mortar and pestle in a nitrogen-filled glove bag, washed with methanol (450 mL) in air, and dried under vacuum at 100 degrees Centigrade to give 113 grams (97% yield) of a product identified by X-ray powder diffractometry to be $Ca_8Si_4O_{12}Cl_8$. The product is a white hygroscopic solid, stable to handling in air and storage in a closed container, and is readily soluble in dilute HCl.

EXAMPLE 2

A Preparation of $Ca_8Si_4O_{12}Cl_8$ from Quartz and $CaCO_3$

A mixture of alpha-quartz ($-325$ mesh, 9.00 grams, 0.150 mole), $CaCO_3$ 15.0 grams, 0.150 mole), and $CaCl_2 \cdot 2H_2O$ (44.1 grams, 0.300 mole) contained in a platinum dish was placed in a horizontal, capped, test-tube shaped ceramic tube near the closed end of the tube. Under a nitrogen gas flow, the part of the assembly containing the mixture was heated slowly to 820 degrees Centigrade and held at this temperature for 24 hours. The container was then cooled to 770 degrees Centigrade and held at this temperature for 48 hours. The nitrogen gas flow was kept at a moderate rate (approximately 250 milliliters/minute) until the rapid evolution of water ceased and then it was reduced to a slower rate (approximately 10 milliliters/minute). The product was removed from the tube, crushed with a mortar and pestle in a nitrogen-filled glove bag, washed with methanol (250 milliliters) in air, and dried under vacuum at 150 degrees Centigrade. The identity of the $Ca_8Si_4O_{12}Cl_8$ product was verified by its X-ray powder pattern. (Yield 33.7 grams, 99%)

EXAMPLE 3

Preparation of Octaethoxycyclotetrasiloxane from $Ca_8Si_4O_{12}Cl_8$

An HCl-ethanol solution (101 mL, 9.12 N) was added over 5 minutes to a slurry of $Ca_8Si_4O_{12}Cl_8$ (100.0 grams, prepared by the method of Example 1., above), ethanol (1.60 L), and toluene (1.80 L), and the resulting mixture was distilled until a substantial amount of distillate (2.74 L) had been collected. The residue was filtered, and the isolated solid was washed with pentane (200 mL). The filtrate and washings were combined, and the solution was reduced by vacuum evaporation to an oil. This oil was mixed with ethanol (250 mL), toluene (250 mL), and an HCl-ethanol solution (6.0 mL, 9.12 N), and the resulting solution was slowly distilled until a substantial amount of distillate (388 mL) had been collected. The residue was vacuum concentrated, and the concentrate was fractionally vacuum distilled (approximately 130 degrees Centigrade, 0.1 torr). An appropriate fraction (38.5 grams) was retained and on the basis of gas chromatography, gas chromatography-mass spectrometry, $^{29}Si$ NMR, and infrared analysis, the major component (86%) of this fraction was found to be octaethoxycyclotetrasiloxane. The contained yield of octaethoxycyclotetrasiloxane was 33 grams, or a 56% yield. The lack of significant OH band in the infrared spectrum of the product showed it was essentially free of silanols.

EXAMPLE 4

Preparation of Octamethylcyclotetrasiloxane from Octaethoxycyclotetrasiloxane A solution of CH$_3$MgCl in tetrahydrofuran (971 mL, 3.07 N, 2.98 mole) was slowly added to a cooled (dry ice/acetone bath) solution of octaethoxycyclotetrasiloxane (approximately 84% purity, 100.0 g., 0.157 mole of contained octaethoxycyclotetrasiloxane prepared by the method of Example 2) in tetrahydrofuran (1.50 L). While being stirred, the resulting mixture was warmed to a somewhat higher temperature (ice bath) and held at this temperature for 48 hours. The reaction product was concentrated under vacuum (ambient temperature), and the residue was vigorously stirred with a mixture of aqueous HCl (2.00 L, 2.98 N) and pentane (1.50 L). After the organic and aqueous phases had been separated, the organic phase was washed with aqueous NaCl (100 mL, 20 wt % NaCl) and then vacuum concentrated and distilled until it had been substantially reduced in volume. The residual liquid (44.7 g) was flash chromatographed in two portions (4×23 cm, 40 micron silica gel, J. T. Baker Chemical Co., Phillipsburg, NJ, hexanes), and the eluate was fractionally distilled. A selected fraction of the distillate was partially fractionally redistilled, and the remaining oil was retained (17.9 g).

This oil was examined by gas chromatography, gas chromatography-mass spectrometry, and infrared spectroscopy. The chromatographic retention time and the mass-spectral fragmentation pattern of the main component were compared to those of authentic octamethylcyclotetrasiloxane, and the infrared spectrum of the whole product was compared to that of this same compound. From the results, it was concluded that this component was octomethylcyclotetrasiloxane. The chromatographic area count data showed that this component constituted most (95%) of the product. The contained yield of octamethylcyclotetrasiloxane was 17 grams, or a 37% yield.

That which is claimed is:

1. A process comprising:
   (A) mixing wollastonite with an alkaline metal halide or alkaline metal halide hydrate, or mixture thereof;
   (B) calcining the mixture; and
   (C) isolating the alkaline metal cyclic silicate halide salt.

2. The process of claim 1 wherein the mixture of wollastonite and the alkaline hydrate or alkaline halide hydrate or mixture thereof is heated to a temperature in the range of 400 to 1300 degrees Centigrade.

3. The process of claim 2 wherein the cation of the alkaline metal halide or alkaline metal halide hydrate is selected from the group consisting of strontium, lithium, magnesium, barium, sodium, potassium, and calcium.

4. The process of claim 3 wherein the halogen of the metal silicate halide salt is selected from the group consisting of fluorine, chlorine, bromine, and iodine.

5. The process of claim 4 wherein the metal silicate halide salt has the cyclic ion of the formula [Si$_4$O$_{12}$]$^{8-}$.

6. The process of claim 5 wherein the alkaline metal silicate halide salt is of the formula Ca$_8$Si$_4$O$_{12}$Cl$_8$.

7. The process of claim 5 further comprising:
   (D) treating the alkaline metal cyclic silicate halide salt with an anhydrous or aqueous acidic alcoholic solution, wherein the alcohol of the acidic alcoholic solution has 1 to 8 carbon atoms, and wherein the acid used to acidify the acidic alcoholic solution is selected from the group consisting of organic and inorganic acids, to form an alcoholic mixture;
   (E) removing low-boiling components from said alcoholic mixture; and,
   (F) isolating from the alcoholic mixture in (E) an alkoxycyclotetrasiloxane of the general formula

[(RO)$_2$SiO]$_4$ wherein, R is an alkyl or aryl group of 1 to 8 carbon atoms.

8. The process of claim 7 wherein the alcohol in the acidic alcoholic solution is selected from the group consisting of methanol, ethanol, n-propanol, isopropanol, n-butanol, and sec-butanol.

9. The process of claim 8 wherein the acid used to acidify the acidic alcoholic solution is hydrochloric acid.

10. The process of claim 9 wherein the alkaline metal cyclic silicate halide salt is of the formula Ca$_8$Si$_4$O$_{12}$Cl$_8$.

11. The process of claim 7 further comprising:
    (G) treating the alkoxycyclotetrasiloxane with a solution of a Grignard alkylating reagent selected from the group of Grignard alkylating reagents represented by the formula R$^1$MgX, where R$^1$ represents an alkyl group of 1 to 10 carbon atoms, and X represents chlorine or bromine; and
    (H) isolating an alkylcyclotetrasiloxane having the general formula

[(R$^1$)$_2$SiO]$_4$ wherein, R$^1$ is an alkyl group of 1 to 10 carbon atoms.

12. The process of claim 11 wherein the alcohol in the acidic alcoholic solution is selected from the group consisting of methanol, ethanol, n-propanol, isopropanol, n-butanol, and sec-butanol.

13. The process of claim 12 wherein the alkaline metal silicate halide salt is of the formula C$_8$Si$_4$O$_{12}$Cl$_8$.

14. A process as claimed in claim 13 wherein the Grignard alkylating reagent is CH$_3$MgCl and the resulting alkylcyclotetrasiloxane is of the formula [(CH$_3$)$_2$SiO]$_4$.

15. A process as claimed in claim 14 wherein the alcohol is ethanol.

16. The process of claim 7 further comprising:
    (G) treating the alkoxycyclotetrasiloxane with a solution of a Grignard arylating reagent selected from the group of Grignard arylating reagents represented by the formula R$^3$MgX, where R$^3$ represents an aryl group of 6 to 10 carbon atoms, and X represents chlorine or bromine; and
    (H) isolating an arylcyclotetrasiloxane having the general formula

[(R$^3$)$_2$SiO]$_4$ wherein, R$^3$ is an aryl group of 6 to 10 carbon atoms.

17. A process comprising:
    (A) mixing a silicate precursor selected from the group consisting of a mixture of an alkaline metal silicate and silica; silica and alkaline metal carbonate or oxide, with an alkaline halide, alkaline halide hydrate, or mixture thereof;
(B) calcining the mixture; and
(C) isolating the alkaline metal cyclic silicate halide salt.

18. The process of claim 17 wherein the cation of the metal silicate halide salt is selected from the group consisting of strontium, lithium, magnesium, barium, sodium, potassium, and calcium.

19. The process of claim 17 further comprising:
(D) treating the alkaline metal cyclic silicate halide salt with anhydrous or aqueous acidic alcoholic solution, wherein the alcohol of the acidic alcoholic solution has 1 to 8 carbon atoms, and wherein the acid used to acidify the acidic alcoholic solution is selected from the group consisting of organic and inorganic acids, to form an alcoholic mixture;
(E) removing low-boiling components from said alcoholic mixture; and,
(F) isolating from the alcoholic mixture an alkoxycyclotetrasiloxane of the general formula $[(RO)_2SiO]_4$ wherein R is an alkyl group of 1 to 8 carbon atoms.

20. The process of claim 19 further comprising:
(G) treating the alkoxycyclotetrasiloxane with a solution of a Grignard reagent represented by the formula $R^2MgX$, where $R^2$ represents an alkyl group of 1 to 10 carbon atoms, or an aryl group of 6 to 10 carbon atoms, and X represents chlorine or bromine; and
(H) isolating the alkylcyclotetrasiloxane having the general formula $[(R^2)_2SiO]_4$ wherein, $R^2$ is as defined above.

21. A process comprising:
(A) treating an alkaline metal cyclic tetrasilicate halide salt with an anhydrous or aqueous acidic alcoholic solution, wherein the alcohol of the acidic alcoholic solution has 1 to 8 carbon atoms, and wherein the acid used to acidify the acidic alcoholic solution is selected from the group consisting of organic and inorganic acids, to form an alcoholic mixture;
(B) removing low-boiling components from said alcoholic mixture; and
(C) isolating from the alcoholic mixture, an alkoxycyclotetrasiloxane of the general formula $[(RO)_2SiO]_4$, wherein R is an alkyl group of 1 to 8 carbon atoms.

* * * * *

UNITED STATES PATENT AND TRADEMARK OFFICE
CERTIFICATE OF CORRECTION

PATENT NO. : 4,824,985

DATED : April 25, 1989

INVENTOR(S) : Goodwin, George B., and Kenney, Malcolm E.

It is certified that error appears in the above-identified patent and that said Letters Patent is hereby corrected as shown below:

On the title page, item [73]

Correct Assignee to:

-- CASE WESTERN RESERVE UNIVERSITY
        Cleveland, Oh.--.

Signed and Sealed this

Ninth Day of January, 1990

Attest:

JEFFREY M. SAMUELS

*Attesting Officer*    *Acting Commissioner of Patents and Trademarks*